(12) United States Patent
Charles

(10) Patent No.: US 11,696,851 B2
(45) Date of Patent: Jul. 11, 2023

(54) CANNULA SYSTEM WITH RETENTION FEATURE

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 471 days.

(21) Appl. No.: 16/829,223

(22) Filed: Mar. 25, 2020

(65) Prior Publication Data

US 2020/0337901 A1 Oct. 29, 2020

Related U.S. Application Data

(60) Provisional application No. 62/838,576, filed on Apr. 25, 2019.

(51) Int. Cl.
*A61F 9/007* (2006.01)
*A61B 17/34* (2006.01)
*A61B 17/02* (2006.01)
*A61M 25/02* (2006.01)

(52) U.S. Cl.
CPC ...... *A61F 9/00781* (2013.01); *A61B 17/0231* (2013.01); *A61B 17/3421* (2013.01); *A61B 2017/3492* (2013.01); *A61F 2250/0018* (2013.01); *A61M 25/02* (2013.01)

(58) Field of Classification Search
CPC .......... A61M 2025/0286; A61M 5/158; A61M 2005/1586; A61M 25/02; A61M 2025/0213; A61M 2025/0246; A61M 2025/0266; A61M 2025/0273; A61M 2025/028; A61M 2025/0293; A61M 37/0015; A61M 2037/0023; A61M 2037/003; A61M 2037/0038; A61M 2037/0046; A61M 2037/0053; A61M 2037/0061
See application file for complete search history.

(56) References Cited

U.S. PATENT DOCUMENTS

| | | | |
|---|---|---|---|
| 1,099,668 A | 6/1914 | Rosenberg | |
| 2,026,686 A | 1/1936 | Kirley | |
| 4,164,943 A * | 8/1979 | Hill | A61M 25/02 604/174 |

(Continued)

FOREIGN PATENT DOCUMENTS

WO 2015184173 A1 12/2015

*Primary Examiner* — Adam Marcetich
(74) *Attorney, Agent, or Firm* — Patterson + Sheridan, LLP

(57) ABSTRACT

Certain embodiments provide a cannula system with a retention mechanism comprising a cannula, a hub coupled to the cannula, wherein a distal end of the cannula is configured to be inserted into a body part up to the hub, and a retention mechanism configured to create resistance for retaining the cannula inside the body part in response to force exerted on the cannula for pulling the cannula out of the body part. The retention mechanism may include retention elements coupled to a bottom surface of the hub, and by rotating the hub in a first direction, the one or more retention elements that are parallel to a surface of the body part are configured to penetrate the body part. In other embodiments, the retention mechanism may include halfpipe elements that pivot on fulcrum points to hold or release the hub and cannula from the body part.

12 Claims, 2 Drawing Sheets

(56) References Cited

U.S. PATENT DOCUMENTS

| | | | |
|---|---|---|---|
| 4,281,659 A * | 8/1981 | Farrar | A61B 5/1482 600/351 |
| 4,617,692 A | 10/1986 | Bond | |
| 4,708,552 A | 11/1987 | Bustos | |
| 4,936,306 A * | 6/1990 | Doty | A61B 5/377 600/382 |
| 5,683,378 A * | 11/1997 | Christy | A61B 17/3423 606/1 |
| 5,692,864 A | 12/1997 | Powell | |
| 6,050,988 A * | 4/2000 | Zuck | A61N 1/303 604/20 |
| 6,186,716 B1 | 2/2001 | West | |
| 6,551,291 B1 * | 4/2003 | de Juan, Jr. | A61F 9/00727 604/289 |
| 8,062,260 B2 | 11/2011 | McCawley | |
| 8,062,305 B2 | 11/2011 | Wenchell | |
| 8,092,423 B2 | 1/2012 | Gresham | |
| 8,277,418 B2 | 10/2012 | Lopez | |
| 9,730,834 B2 | 8/2017 | Charles | |
| 2002/0058925 A1 * | 5/2002 | Kaplan | A61M 25/0662 606/151 |
| 2004/0073231 A1 | 4/2004 | Juan | |
| 2006/0110428 A1 * | 5/2006 | deJuan | A61L 27/54 424/427 |
| 2006/0235445 A1 * | 10/2006 | Birk | A61M 39/0208 606/151 |
| 2007/0161964 A1 * | 7/2007 | Yuzhakov | A61M 37/0015 604/272 |
| 2007/0212397 A1 * | 9/2007 | Roth | A61F 9/0017 604/890.1 |
| 2008/0177239 A1 | 7/2008 | Li | |
| 2008/0294174 A1 * | 11/2008 | Bardsley | A61B 17/3415 606/186 |
| 2010/0217198 A1 * | 8/2010 | Franklin | A61B 17/072 604/175 |
| 2011/0196394 A1 * | 8/2011 | Harders | A61B 5/0056 606/157 |
| 2013/0116523 A1 * | 5/2013 | Jung | A61M 5/00 604/9 |
| 2014/0276658 A1 * | 9/2014 | Ward | A61M 25/02 604/541 |
| 2014/0277056 A1 * | 9/2014 | Poore | A61B 17/3417 606/190 |
| 2014/0316326 A1 * | 10/2014 | Behar-Cohen | A61F 9/0026 604/21 |
| 2016/0051335 A1 * | 2/2016 | Richmond | A61B 90/36 600/249 |
| 2016/0067083 A1 * | 3/2016 | Lue | A61F 9/0017 606/107 |
| 2016/0106461 A1 | 4/2016 | Morris | |
| 2016/0296221 A1 | 10/2016 | Morris | |
| 2017/0135639 A1 * | 5/2017 | Sun | A61B 5/6839 |
| 2017/0197028 A1 * | 7/2017 | Goldsmith | A61M 39/0247 |
| 2018/0021061 A1 | 1/2018 | Reid | |
| 2018/0311073 A1 * | 11/2018 | Alhourani | A61F 9/007 |
| 2018/0353326 A1 | 12/2018 | Hallen | |
| 2019/0053825 A1 | 2/2019 | Ochoa | |
| 2019/0314012 A1 * | 10/2019 | Bertollo | A61B 90/06 |
| 2021/0060302 A1 * | 3/2021 | Bertollo | A61M 25/02 |

\* cited by examiner

CANNULA SYSTEM WITH RETENTION FEATURE

PRIORITY CLAIM

This application claims the benefit of priority of U.S. Provisional Patent Application Ser. No. 62/838,576 titled "CANNULA SYSTEM WITH RETENTION FEATURE," filed on Apr. 25, 2019, whose inventor is Steven T. Charles, which is hereby incorporated by reference in its entirety as though fully and completely set forth herein.

TECHNICAL FIELD

The present disclosure relates generally to a cannula system with a retention feature.

BACKGROUND

A cannula system generally includes a cannula hub ("hub") and a tube-shaped cannula that can be inserted through a small incision or puncture made on a body part. Different types of cannulas may be used for different purposes. For example, in ophthalmic surgery, an infusion cannula may be used for administration of therapeutic fluids, gases or silicone oil to a patient's eye. To use an infusion cannula, a surgeon makes an incision in the eye and inserts the cannula into the incision up to the hub, which acts as a stop, preventing the cannula from entering the eye completely. The hub of the infusion cannula is generally coupled to a tube, such as a plastic tube, through which fluids can be administered to the eye. An infusion cannula may be used during vitrectomy, which is a surgical procedure where the vitreous humor gel that fills the eye cavity is removed to provide better access to the retina. Other types of cannulas (referred to as "protective cannulas" herein) may also include cannulas that are inserted into an incision, made in the eye, to protect the incision's sidewalls from repeated contact by instruments that are inserted into and removed from the cannula.

In certain cases, cannulas may be inadvertently pulled partially or all the way out of the patient's eye. For example, an infusion cannula may be pulled when the attached tubing is inadvertently pulled by, for example, a surgical assistant. Pulling an infusion cannula, in some cases, may result in a suprachoroidal or subretinal infusion of fluids as well as secondary bleeding. The suprachoroidal space is a potential space between the sclera and choroid that traverses the circumference of the posterior segment of the eye. The subretinal space between the photoreceptors and the retinal pigment epithelium (RPE) is the remnant of the embryonic optic vesicle. Infusing fluids into the suprachoroidal or subretinal spaces may cause damage to the eye.

Protective cannulas may also be inadvertently pulled upon removing instruments inserted therein, such as flexible laser probes, partially open scissors, forceps, etc. from the cannula. Once the cannula is pulled, if the eye has a thin sclera (such as in myopic patients or patients with the Marfans syndrome), it may be difficult to reinsert the protective cannula in the eye. Also, as a result of an inadvertent removal of a protective cannula, chemosis may occur. Chemosis refers to the swelling or edema of the conjunctiva on the eye.

BRIEF SUMMARY

The present disclosure relates generally to a cannula system with a retention feature.

Certain embodiments provide a cannula system with a retention mechanism comprising a cannula having a proximal end and a distal end, a hub coupled to the cannula, wherein the distal end of the cannula is configured to be inserted into a body part up to the hub, and a retention mechanism configured to create resistance for retaining the cannula inside the body part in response to force exerted on the cannula for pulling the cannula out of the body part. In certain embodiments, the retention mechanism comprises one or more retention elements coupled to a bottom surface of the hub, and by rotating the hub in a first direction, the one or more retention elements that are parallel to a surface of the body part are configured to penetrate the body part. In other embodiments, the retention mechanism may include at least two halfpipe elements that each have an outer-eye segment, an inner-eye segment, and a fulcrum point. The at least two halfpipe elements may be coupled to both the cannula and the hub at the fulcrum points. The outer-eye segments may be coupled together at the fulcrum points through a first extensible element, and the outer-eye segments may be coupled together on an opposing side of the outer-eye segments from the fulcrum points with a second extensible element. In some embodiments, when the retention elements are in a deployed position, the two extensible elements may exert a force on the outer-eye segments to keep the outer-eye segments substantially parallel such that inner surfaces of the outer-eye segments are touching outer surfaces of the cannula and the inner-eye segments are spread to retain the retention mechanism in the eye. Further, when the retention elements are in an un-deployed position, outer-eye segments may be spread while the inner-eye segments are flush with the outer surfaces of the cannula so that the retention mechanism can be removed from the eye.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments, it should be understood that such exemplary embodiments can be implemented in various devices, instruments, and methods.

Aspects of the present disclosure provide various alternative embodiments of a cannula system with a retention feature or element(s). Using a cannula with a retention feature helps prevent an inadvertent removal of the cannula, thereby, preventing the disastrous outcomes associated with the inadvertent removal. Note that although certain embodiments herein are described with respect to cannula systems that are used for insertion into a patient's eye, the scope of this disclosure is not limited to ophthalmic surgeries. For example, the retention elements described herein can be used in conjunction with cannulas that are used for surgeries on other body parts.

Figure 1:
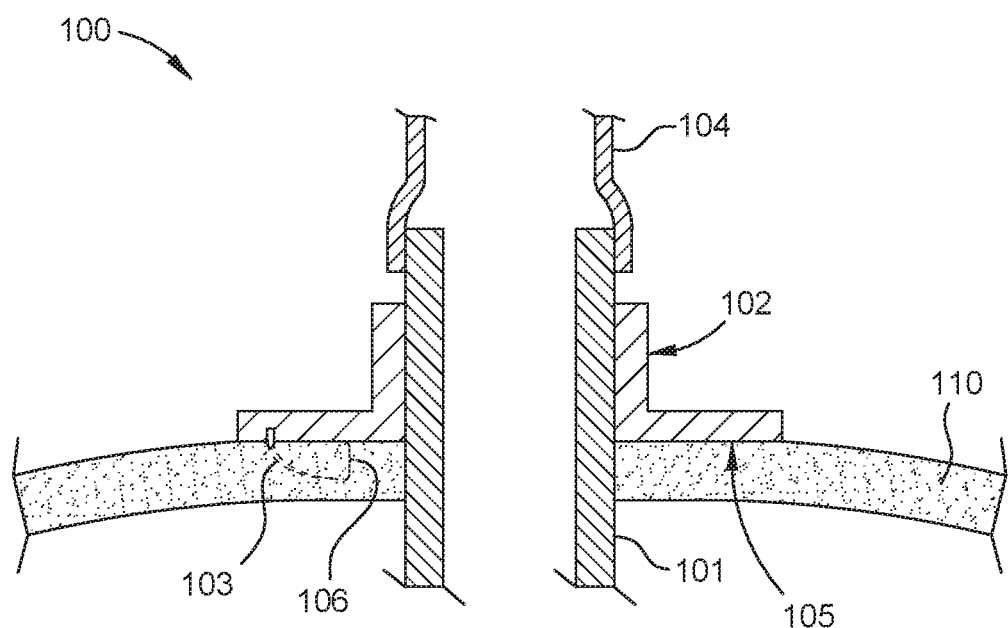
FIG. 1 illustrates a cross-sectional view of an example cannula system with a cannula that is coupled to a hub with a retention element, in accordance with certain embodiments.

FIG. 1 illustrates a cross-sectional view of an example cannula system 100 comprising cannula 101 that is coupled to a hub 102 with a retention element 103. As shown, cannula 101 is inserted into an eye 110 such that the bottom surface 105 of hub 102 is flush with the surface of eye 110 (i.e., the surface of the outermost layer of the eye, referred to as the sclera). In the example FIG. 1, cannula 101 is an infusion cannula coupled to tube 104, through which materials, such as fluids, are infused into eye 110. Note that the shape of hub 102 is exemplary. Other shapes, such as a ring-shaped or cylindrical hub, may be used in other embodiments.

As shown, retention element 103 is coupled to bottom surface 105 of hub 102. In the example of FIG. 1, retention element 103 is a curved needle that extends from bottom surface 105 down to a certain depth, shown as depth 106. In certain embodiments, depth 106 may range from 200 to 600 microns. Retention element 103 is illustrated in dashed lines because, in reality, the tip of retention element is not directed towards or perpendicular to cannula 101. Instead the tip of retention element 103 is parallel or almost parallel to cannula 101 and the outer curvature of the hub 102, as further shown in FIG. 2.

When retention element 103 is placed on and flush with the surface of eye 110, rotating hub 102, towards where the tip of retention element 103 is directed to, causes retention element 103 to bite or penetrate into the one or more outermost layers of eye 110, such as the sclera. For example, a user, such as a surgeon, may rotate hub 102 in a clock-wise manner (e.g., using fingers or a surgical instrument, such as forceps), causing the tip of retention element 103 to penetrate eye 110. By continuing to rotate hub 102, retention element 103 penetrates deeper into eye 110 until bottom surface 105 is completely flush with the outer surface of eye 110, as shown in FIG. 1. Once bottom surface 105 of hub 102 completely touches the outer surface of eye 110, the tip of retention element 103 has penetrated into the eye at depth 106. In other words, FIG. 1 illustrates a state of cannula system 100 where retention element 103 has completely penetrated eye 110 and bottom surface 105 is completely flush with the outer surface of eye 110. In one example, depth 106 may correspond to half of the depth of eye 110's sclera. When removing cannula 101 from eye 110, a surgeon may rotate hub 102 in a counter clockwise manner to withdraw retention element 103 from eye 110. Although only a single retention element 103 is shown in FIG. 1, hub 102 comprises additional retention elements 103, which are visible in a different view that is depicted in FIG. 2.

Figure 2:
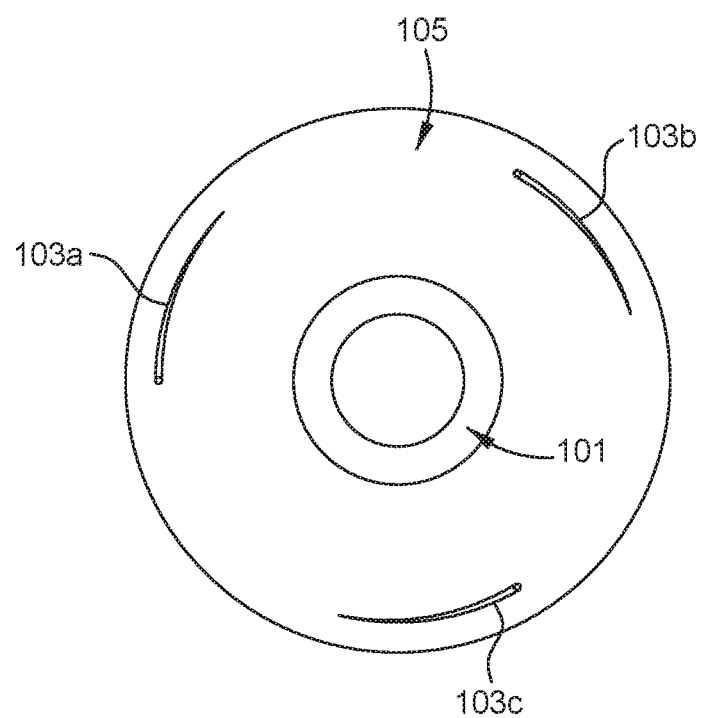
FIG. 2 illustrates a bottom surface of the hub of FIG. 1 with three retention elements, in accordance with certain embodiments.

FIG. 2 illustrates bottom surface 105 of hub 102 having three identical equidistant retention elements 103a-103c (collectively referred to as retention elements 103). Although not clear from FIG. 2, which illustrates a two-dimensional view of bottom surface 105, retention elements 103 extend out from bottom surface 105, such that there is a distance or depth 106 (shown in FIG. 1), between the tip of each retention element 103 and bottom surface 105. As shown, retention elements 103 have the same curvature (e.g., or the same curvature vector) as the hub 102, such that retention elements 103 extend and curve in a manner that is parallel to how hub 102 curves (e.g., concentric with an outer diameter of hub 102). Note that although FIG. 2 shows three identical equidistant retention elements 103, retention elements 103 may neither be identical nor equidistant.

Different manufacturing techniques may be used to couple retention elements 103 to hub 102. For example, retention elements 103 may be inserted and locked into holes, made in bottom surface 105, using friction locking. Retention elements 103 prevent an inadvertent removal of cannula 101 as a result of a pull force exerted on cannula 101, such as when tube 104 is pulled. This is because cannula 101 can only be smoothly removed from eye 110 by rotating hub 102.

Note that although hub 102 is shown with three retention elements 103, any number of retention elements 103 may be used. Also, in the example of FIG. 1, cannula 101 is an infusion cannula. However, retention elements, that are identical or similar to retention elements 103, may be used in conjunction with other types of cannulas, such as protective cannulas. Protective cannulas, in certain examples, differ from infusion cannulas in that the proximal end of a protective cannula terminates at the hub and does not extend proximally outside the hub. Similar to infusion cannulas, in a protective cannula, retention elements 103 are coupled to the bottom surface of the hub. When inserting the cannula into the eye, the surgeon rotates the hub to allow retention elements 103 to penetrate into the eye. As a result, retention elements 103 help prevent an inadvertent removal of the protective cannula from the eye. Note that although FIGS. 1 and 2 illustrate retention elements 103 as being coupled to the bottom surface of the hub, in certain aspects, one or more retention elements, that operate similar to retention elements 103, may be coupled to the sides of the hub.

Figure 3A:
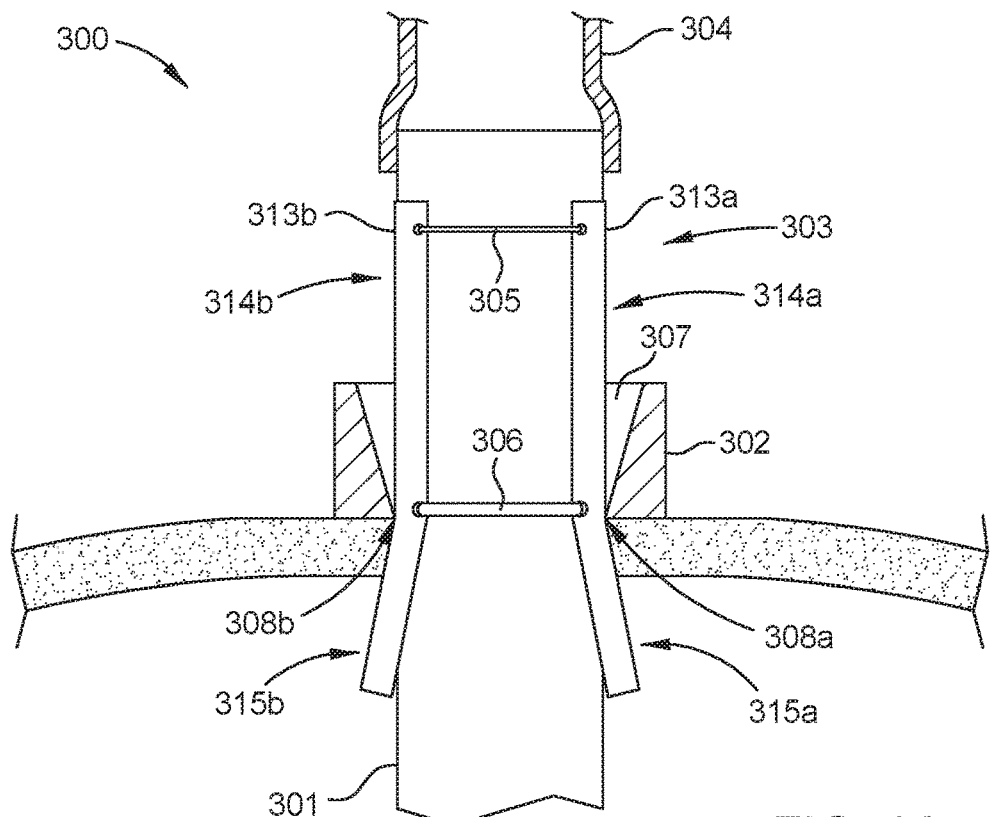
FIG. 3A illustrates an example cannula system with a cannula coupled to a retention element in a deployed state, in accordance with certain embodiments.
Figure 3B:
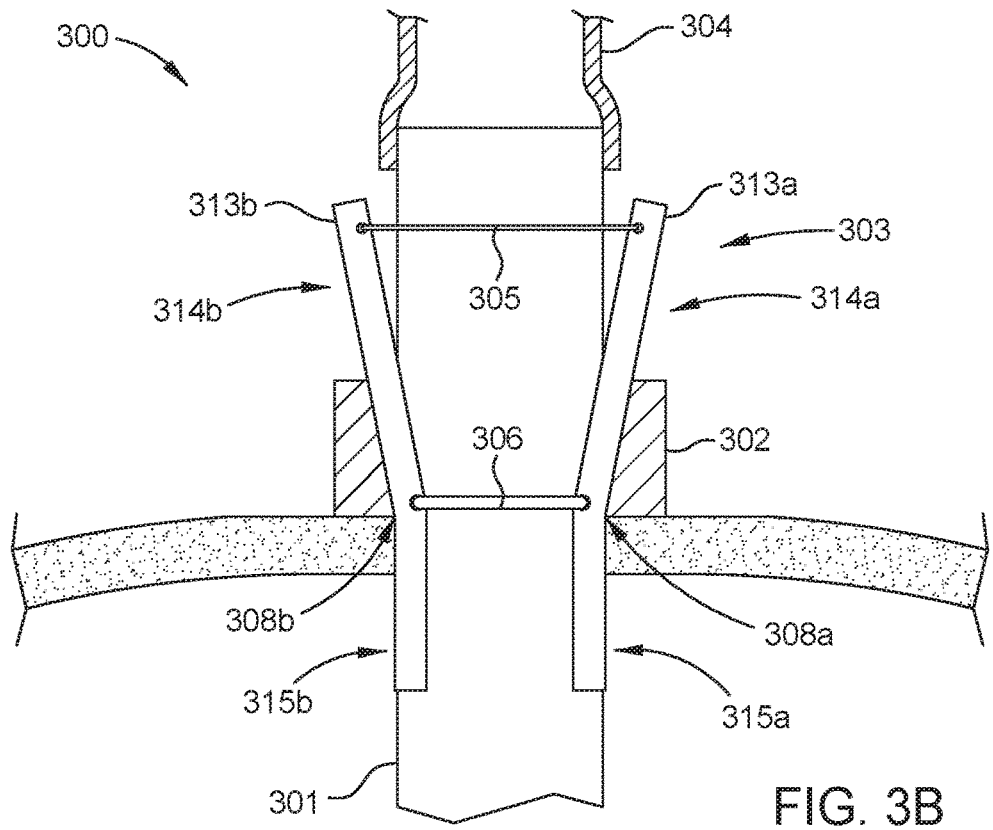
FIG. 3B illustrates an example cannula system with a cannula coupled to a retention element in an un-deployed state, in accordance with certain embodiments.

FIGS. 3A and 3B illustrate another example retention element used in conjunction with a cannula to help prevent an inadvertent removal of the cannula from the eye. For example, in some embodiments, the retention mechanism described herein may be configured to be deployed translimbal for anterior segment surgery (other body locations and surgery types are also contemplated). FIG. 3A shows a cannula system 300 with a cannula 301 and hub 302 that are coupled to a retention element 303 in a deployed state. As further described below, retention element 303 comprises two halfpipe-shaped elements ("halfpipe elements") 313a and 313b (collectively referred to as halfpipe elements 313), extendible elements 305 and coupling elements 306. Hub 302 is cylindrical or ring-shaped and at its distal end is coupled to retention element 303. More specifically, hub 302 is attached to and surrounds the entire circumference of retention element 303. Various techniques may be used for coupling retention element 303 and hub 302. In one example, adhesives may be used. In certain embodiments, hub 302 and retention element 303 may manufactured as a single part (e.g., instead of being two parts that are coupled together). As shown, hub 302 has a trapezoidal-shaped cavity or hole 307, which allows retention element 303 to operate as described below. Note that FIGS. 3A and 3B illustrate an example of an infusion cannula 301 that is attached to tube 304. However, retention element 303 may be used in conjunction with other types of cannulas, such as protective cannulas. Also, note that FIG. 3A illustrates a cross sectional view of eye 110, hub 302, and tube 304, while retention element 303 and cannula 301 are not illustrated in a cross-sectional manner for illustrative purposes.

As discussed, retention element 303 comprises two halfpipe elements 313. Each halfpipe element 313 comprises an outer-eye segment ("outer segment") 314, an inner-eye segment ("inner segment") 315, and fulcrum point 308. Outer segments 314a-314b (collectively referred to as outer segments 314) are segments that are completely or at least substantially located outside of eye 110. Inner segments 315a-315b (collectively referred to as inner segments 315) are segments that are completely or at least substantially inserted into and operate inside eye 110. Each halfpipe element 313 acts similar to a lever and pivots at its corresponding fulcrum point 308, which acts as support. For example, FIG. 3A illustrates retention element 303 in a deployed position such that the inner segments 315 of halfpipe elements 313 are spread out while the outer segments 314 are in a cylindrical state and touching cannula 301. In contrast, FIG. 3B, which is described in further detail below, illustrates retention element 303 in an un-deployed position such that that the inner segments 315 of halfpipe elements 313 are cylindrical and touching cannula 301 while the outer segments 314 are spread out. Note that FIGS. 3A and 3B illustrate only one side of halfpipe elements 313. The opposite side of halfpipe elements 313 are identical to the side that is shown in FIGS. 3A and 3B. Note that the length of inner segments 315 may vary in different embodiments. In one example, inner segments 315 may be tall enough to ensure that the distal of ends of inner segments 315 are positioned in the vitreous humor.

As shown in FIG. 3A, outer segments 314a-314b are coupled together using a flexible or extendable element ("extensible element") 305. An identical extensible element 305 is also used to couple outer segments 314 together on the opposite side. In one example, extensible element 305 is made out of rubber material or other elastic material. (e.g., silicone rubber) The two extensible elements 305 that are coupled to the two sides of outer segments 314 exert enough force on outer segments 314 to keep them parallel such that the inner surface of outer segments 314 are completely or at least substantially touching or flush with the surfaces of the outer sides of cannula 301, when retention element 303 is in its deployed position, as shown in FIG. 1A. When outer segments 314 are cylindrical, as described above, retention element 303 is in its deployed position. In addition to extensible elements 305, halfpipe elements 313 are also coupled together using coupling elements 306. Note that FIG. 1A only shows one coupling element 306, however, an identical coupling element 306 is used for coupling halfpipe elements 313 on the opposite side. In certain aspects, coupling elements 306 are made from material that is more rigid as compared to material that is used for manufacturing extensible elements 305. For example, coupling elements 306 may be made from material such as stainless steel, polyetheretherketone (PEEK), etc. Coupling elements 306 are configured to clamp halfpipe elements 313 to cannula 301 at fulcrum points 308a-308b (collectively referred to as fulcrum points 308), such that halfpipe elements 313 are always touching cannula 301 at corresponding fulcrum points 308. Using coupling elements 306 limits the movements of halfpipe elements 313 to only pivoting at corresponding fulcrum points 308 instead of other types of movements such as scissors-like movements. Note that hub 302 and halfpipe elements 313 are coupled together and/or touch at fulcrum points 308 as well. In certain aspects, hub 302 and halfpipe elements 313 may be coupled together at fulcrum points 308 in order to ensure that cannula 301 and halfpipe elements 313 do not slide or move upward or downward through and with respect to hub 102.

When it is at-rest, retention element 303 is deployed, because extendible elements 305 exert enough pull force to keep outer segments 314 parallel and clamp them to cannula 101, which means the inner segments 315 are spread. In its deployed position, retention element 303 helps prevent any inadvertent removal of cannula 301. When inner segments 315 are spread, a larger amount of force is required to remove cannula 301 from eye 110 as opposed to when inner segments 315 are cylindrical. To pull cannula 301 out of eye 110 when retention element is deployed, enough pull force should be applied to cannula 301 to overcome the force exerted by extendible elements 305 as well as the friction between inner segments 315 and the layers of the eye.

FIG. 3B illustrates retention element 303 in an un-deployed position. As shown, in an un-deployed position, outer segments 314 are spread while inner segments 315 are parallel such that the inner surface of inner segments 314 are completely or at least substantially flush with the surfaces of the outer sides of cannula 301. As described above, in its at-rest state, retention element 303 is deployed, meaning that outer segments 314 are parallel due to the pull force exerted by extendible elements 305. In order to un-deploy retention element 303, a certain amount of force needs to be exerted to pull outer segments 314 away from each other, as shown in FIG. 3B. A surgical instrument such as specialized forceps may be used for this purpose. As shown, the trapezoid-shaped hole 307 within hub 102 allows for outer segments 214 to spread or pivot around fulcrum points 308.

Because cannula 301 cannot be inserted into eye 110 when retention element 303 is deployed, prior to inserting cannula 301 a surgeon may use the specialized forceps to un-deploy retention feature 303, thereby ensuring that inner segments 315 are parallel or cylindrical, as shown in FIG. 3B. In an un-deployed position, retention element 303 can be inserted along with cannula 301 into eye 110. Once cannula 301 and retention element 303 are inserted into eye 110, the surgeon may release outer segments 314 by removing the specialized forceps, thereby causing retention element 303 to be deployed. Similarly, prior to removing cannula 301 from eye 110, the surgeon may again un-deploy retention element 303 to allow cannula 301 to be smoothly removed from eye 110 without unnecessary force or causing possible injury, such as a further opening of the incision.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A cannula system, comprising:
a cannula comprising a proximal end and a distal end;
a hub coupled to the cannula, wherein:

the distal end of the cannula is configured to be inserted into an eye and extend distally beyond a bottom surface of the hub, the bottom surface of the hub is configured to be flush with a surface of the eye when the distal end of the cannula is inserted into the eye, the hub comprises one or more retention elements coupled to the bottom surface of the hub to create resistance for retaining the cannula inside the eye in response to force exerted on the cannula for pulling the cannula out of the eye, and by rotating the hub in a first direction, the one or more retention elements are configured to penetrate the eye.

2. The cannula system of claim 1, wherein the one or more retention elements are curved.

3. The cannula system of claim 2, wherein each of the one or more retention elements comprises a curved needle.

4. The cannula system of claim 1, wherein each of the one or more retention elements has a curvature that is concentric with a curvature of the hub.

5. The cannula system of claim 1, wherein the one or more retention elements comprise three identical and equidistant retention elements.

6. The cannula system of claim 1, wherein by rotating the hub in a second direction, the one or more retention elements are configured to be removed from the eye.

7. A cannula system, comprising:
a cannula comprising a proximal end and a distal end;
a hub coupled to the cannula, wherein:

the distal end of the cannula is configured to be inserted into an eye and extend distally beyond a bottom surface of the hub, the bottom surface of the hub is configured to be flush with a surface of the eye when the distal end of the cannula is inserted into the eye, the hub comprises one or more retention elements coupled to the bottom surface of the hub to create resistance for retaining the cannula inside the eye in response to force exerted on the cannula for pulling the cannula out of the eye, and by rotating the hub in a first direction, a tip of each of the one or more retention elements is configured to penetrate a sclera layer of the eye at a half depth of the sclera layer.

8. The cannula system of claim 7, wherein the one or more retention elements are curved.

9. The cannula system of claim 8, wherein each of the one or more retention elements comprises a curved needle.

10. The cannula system of claim 7, wherein each of the one or more retention elements has a curvature that is concentric with a curvature of the hub.

11. The cannula system of claim 7, wherein the one or more retention elements comprise three identical and equidistant retention elements.

12. The cannula system of claim 7, wherein by rotating the hub in a second direction, the one or more retention elements are configured to be removed from the eye.

* * * * *